United States Patent
Krishna et al.

(10) Patent No.: US 11,247,956 B2
(45) Date of Patent: Feb. 15, 2022

(54) CATALYTIC PRODUCTION OF 1,2,5,6-HEXANETETROL FROM LEVOGLUCOSENONE

(71) Applicant: Wisconsin Alumni Research Foundation, Madison, WI (US)

(72) Inventors: Siddarth H. Krishna, Madison, WI (US); George W. Huber, Middleton, WI (US); James A. Dumesic, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/049,241

(22) PCT Filed: Apr. 19, 2019

(86) PCT No.: PCT/US2019/028360
§ 371 (c)(1),
(2) Date: Oct. 20, 2020

(87) PCT Pub. No.: WO2019/204753
PCT Pub. Date: Oct. 24, 2019

(65) Prior Publication Data
US 2021/0130269 A1    May 6, 2021

Related U.S. Application Data

(60) Provisional application No. 62/660,517, filed on Apr. 20, 2018.

(51) Int. Cl.
| | |
|---|---|
| *C07C 29/17* | (2006.01) |
| *C07C 29/132* | (2006.01) |
| *C07C 31/24* | (2006.01) |
| *B01J 21/12* | (2006.01) |
| *B01J 23/42* | (2006.01) |
| *B01J 23/44* | (2006.01) |
| *B01J 23/46* | (2006.01) |

(52) U.S. Cl.
CPC ............. *C07C 29/175* (2013.01); *B01J 21/12* (2013.01); *B01J 23/42* (2013.01); *B01J 23/44* (2013.01); *B01J 23/462* (2013.01); *B01J 23/464* (2013.01); *C07C 29/132* (2013.01); *C07C 29/172* (2013.01)

(58) Field of Classification Search
None
See application file for complete search history.

(56) References Cited

U.S. PATENT DOCUMENTS

| | | |
|---|---|---|
| 4,820,880 A | 4/1989 | Urbas |
| 8,865,940 B2 | 10/2014 | Allgeier et al. |
| 2013/0172578 A1 | 7/2013 | Allgeier et al. |
| 2013/0172629 A1 | 7/2013 | Allgeier et al. |
| 2013/0231505 A1 | 9/2013 | Allgeier et al. |
| 2014/0228596 A1 | 8/2014 | Allgeier et al. |
| 2014/0228956 A1 | 8/2014 | Weiman |
| 2017/0044123 A1 | 2/2017 | Stensrud et al. |

FOREIGN PATENT DOCUMENTS

WO    WO 2013101980 A1    7/2013

OTHER PUBLICATIONS

Corma, A.; Iborra, S.; Velty, A., Chemical Routes for the Transformation of Biomass into Chemicals. Chemical Reviews 2007, 107(6), 2411-2502.
International Search Report, PCT/US2019/028360, dated Jan. 7, 2019.

*Primary Examiner* — Medhanit W Bahta
(74) *Attorney, Agent, or Firm* — Joseph T. Leone, Esq.; DeWitt LLP

(57) ABSTRACT

A method of making of 1,2,5,6-hexanetetrol ("tetrol"). The method includes the steps of contacting a reaction solution containing water as well as levoglucosenone, dihydrolevoglucosenone, and/or levoglucosanol, with a catalyst containing metal and acid functionalities, at temperature of from about 100° C. to about 175° C., and a hydrogen partial pressure of from about 1 bar to about 50 bar (about 0.1 MPa to about 5 MPa), and for a time wherein at least a portion of the reactant is converted into 1,2,5,6-hexanetetrol.

13 Claims, 2 Drawing Sheets

CATALYTIC PRODUCTION OF 1,2,5,6-HEXANETETROL FROM LEVOGLUCOSENONE

CROSS-REFERENCE TO RELATED APPLICATIONS

Priority is hereby claimed to U.S. provisional patent application Ser. No. 62/660,517, field Apr. 20, 2019, which is incorporated herein by reference.

FEDERAL FILING STATEMENT

This invention was made with government support under DE-EE0006878 awarded by the US Department of Energy. The government has certain rights in the invention.

BACKGROUND

Cellulose is a primary component of plant matter. It is a polysaccharide of the general formula $(C_6H_{10}O_5)_n$ and consists of several hundred to many thousands of $\beta(1\rightarrow 4)$ linked D-glucose units. It is non-nutritive to virtually all mammals, the only exception being ruminants. Large-scale use of processed cellulose itself is limited almost exclusively to making paper, cardboard, and other paper products. To a smaller extent, cellulose is chemically converted to viscose to make extruded, regenerated cellulose products such as cellophane film and rayon fiber. The cellulose content of natural cotton fiber, for example, is around 90%.

Due to its ubiquity, there is a long history of efforts to make more valuable commercial products from cellulose. Cellulose, for example, can be converted to glucose through acid or enzymatic hydrolysis. Cellulose, however, is crystalline and resists hydrolysis. Thus, for hydrolysis to occur in a commercially reasonable time frame, the hydrolysis conditions are harsh. Known acid hydrolysis methods typically require concentrated sulfuric acid to achieve high yields of glucose. Undesired byproducts, including humins and hydroxymethylfurfural, are always a byproduct of this reaction from both series and parallel reactions. Enzymatic hydrolysis methods known in the art for industrial-scale production of glucose from cellulose face challenges due to low reaction rates and the high cost of the enzymes needed.

Several earlier patents and published patent applications describe methods to make 1,2,5,6-hexanetetrol indirectly from sorbitol. Sorbitol is produced by the hydrogenation of glucose. 1,2,5,6-hexanetetrol is known by several other names, including 3,4-dideoxyhexitol, hexane-1,2,5,6-tetrol, 1,2,5,6-tetrahydroxyhexane, and simply tetrol. For sake of brevity, "tetrol" shall be used throughout the remainder of the specification. See, for example, U.S. Pat. Publication US2017/0044123, published Feb. 16, 2017. This publication describes a method to make tetrol in up to 50% yield from sorbitol or an alkyl-glycoside using a Raney copper catalyst. In this method, the reactant is an aqueous solution containing at least 20% wt/wt of a sugar alcohol and/or a methyl- or ethyl-glycoside of a sugar. The reactant solution is contacted with hydrogen and a Raney copper catalyst for a time and at a temperature and pressure sufficient to produce a mixture containing at least 50% mol/mol 1,2,5,6-hexantetrol (i.e. "tetrol"). Alternatively, the reactant solution may comprise 20-30% wt/wt water, 45-55% propylene glycol, and at least 20% wt/wt of a C6 sugar alcohol and/or a methyl- or ethyl-glycoside of a C6 sugar. Again, the reactant solution is contacted with hydrogen and a Raney copper catalyst for a time and at a temperature and pressure sufficient to produce a mixture containing 1,2,5,6-hexanetetrol with a selective yield of at least 35% wt/wt of the desired product.

U.S. Pat. No. 4,820,880, issued Apr. 11, 1989, to Urbas, and assigned to the Michigan Biotechnology Institute, describes a method for making tetrol by hydrogenolysis of hexitols in the presence of a copper chromite $(Cu_2Cr_2O_5)$ catalyst at a pressure of at least 50 atm. The maximum reported yield of tetrol was 38%.

U.S. Pat. No. 8,865,940, issued Oct. 21, 2014, to Allgeier et al., and assigned to E.I. du Pont de Nemours & Company, describes a method for preparing 1,6-hexanediol from renewable resources. The process generally comprises contacting levoglucosenone with hydrogen in the presence of a first hydrogenation catalyst at a first temperature to form an intermediate, and then heating the intermediate in the presence of hydrogen and a second hydrogenation catalyst at a second temperature to form product mixture containing 1,6-hexanediol. The 1,6-hexanediol may optionally be converted into 1,6-diaminohexane. The hydrogenation catalysts are selected from supported platinum catalysts, supported palladium catalysts, supported ruthenium catalysts, supported nickel catalysts, catalysts derived from nickel-aluminum alloys, catalysts derived from cobalt-aluminum alloys, and organophosphorus or organometallic complexes of rhodium, iridium, ruthenium, or titanium.

SUMMARY

Disclosed herein is a method to produce 1,2,5,6-hexanetetrol ("tetrol") from levoglucosanol ("Lgol") in high yield (over 90%) over a catalyst containing metal and acid functionalities. Lgol can be produced in 100% yield from quantitative hydrogenation of levoglucosenone or dihydrolevoglucosenone over a metal catalyst, in methods known in the art. Tetrol is a useful intermediate to produce any number of higher value chemicals, including polymers and it can be used in formulations. According to a 2017 patent application from Archer Daniels Midland discussing the isolation of tetrol from other polyols, "As a useful intermediate in the formation of higher value chemicals, the industrial production of 1,2,5,6-HTO can be commercially important" (US 2017/0066702 A1). Tetrol and other reduced >C4 polyols can be used to produce polyesters, alkyd resins, and polyurethanes (Corma, A.; Iborra, S.; Velty, A., Chemical Routes for the Transformation of Biomass into Chemicals. Chemical Reviews 2007, 107 (6), 2411-2502).

Thus, disclosed herein is a method of making of 1,2,5,6-hexanetetrol. The method comprises contacting a solution comprising levoglucosanol and water with a catalyst comprising a metal hydrogenation catalyst in combination with an acid catalyst. The method is also suitable when levoglucosenone or dihydrolevoglucosenone, the precursors to levoglucosanol, are used as feedstocks. The reaction takes place at moderate temperatures, preferably from about 100° C. to about 175° C. The reaction does require molecular hydrogen $(H_2)$ and is preferably conducted at a hydrogen partial pressure of from about 1 bar to about 50 bar (about 0.1 MPa to about 5 MPa). The concentration of levoglucosanol in the aqueous solution varies from about 1.0 to 50.0 wt %. When the reaction is carried out for a sufficient amount of time, at least a portion of the levoglucosanol (and under ideal circumstances, essentially all of the levoglucosanol) is converted into 1,2,5,6-hexanetetrol.

The preferred catalysts contain metal nanoparticles in combination with acid sites. The preferred metal nanoparticles are metals selected from the group consisting of Ru, Rh, Pd, Os, Ir, Pt, Cu, Ni, Co, and combinations thereof. The noble metals Ru, Rh, Pd, and Pt are more preferred still, with platinum being the most preferred.

The reaction is preferably conducted at a pressure is from about 20 to about 45 bar, with that pressure being supplied by hydrogen.

The method may be conducted using the metal catalyst in combination with any catalyst having acidic sites, without limitation. Preferably, the metal nanoparticles are deposited directly on an acidic support material, although the method is also suitable when the metal and acid components are separated. Preferably, the support is selected from alumina, zirconia, titania, hafnia, silica, silica-alumina, zirconia phosphate, titanium phosphate, zeolites, and mixtures of these. The acid catalyst can also include acidic metal oxides including oxides of manganese, iron, molybdenum, niobium, zirconium, titanium, tungsten, rhenium, tin, or combinations thereof, deposited on an inert support material. The acid catalyst can include homogeneous mineral acids such as sulfuric acid, hydrochloric acid, nitric acid, phosphoric acid, and combinations thereof. In preferred versions of the method, the support comprises aluminum and silicon, with platinum deposited on the support.

The stereochemistry of the product tetrol can be influenced by the stereochemistry of the reaction levoglucosanol. Thus, the method includes conducting the reaction using a reactant solution in which the levoglucosanol has a threo-to-erythro ratio and the threo-to-erythro ratio is about 1, or less than 1, or greater than 1.

The method works equally well when conducted batch-wise or continuously.

More specifically disclosed herein are the following:

1. A method of making of 1,2,5,6-hexanetetrol, the method comprising:
contacting a solution comprising levoglucosenone, dihydrolevoglucosenone, or levoglucosanol, or mixtures thereof and water, with a catalyst containing metal sites and acid sites, at temperature of from about 100° C. to about 175° C., and a hydrogen partial pressure of from about 1 bar to about 50 bar (about 0.1 MPa to about 5 MPa), and for a time wherein at least a portion of the levoglucosenone, dihydrolevoglucosenone, or levoglucosanol, or mixtures thereof is converted into 1,2,5,6-hexanetetrol.

2. The method of Claim 1, wherein the catalyst comprises a metal selected from the group consisting of Ru, Rh, Pd, Os, Ir, Pt, Au, Ag, Cu, Co, Fe, or Ni.

3. The method of Claim 1, wherein the catalyst comprises a noble metal selected from the group consisting of Ru, Rh, Pd, and Pt.

4. The method of Claim 1, wherein the catalyst comprises a noble metal that is platinum.

5. The method of any one of Claims 1 to 4, wherein the pressure is from about 20 to about 45 bar.

6. The method of Claim 5, wherein the pressure is from about 30 to about 40 bar.

7. The method of any preceding claim, wherein the acid catalyst is selected from mineral acids such as sulfuric acid, hydrochloric acid, nitric acid, or phosphoric acid, and solid acidic supports such as alumina, zirconia, titania, hafnia, silica, zirconia-phosphate, titania-phosphate, zirconia-tungsten, titania-tungsten, zeolites, and mixtures of these.

8. The method of any preceding claim, wherein the support comprises aluminum and silicon.

9. The method of Claim 8, wherein the catalyst comprises platinum deposited on the support.

10. The method of any preceding claim, wherein the levoglucosanol has a threo-to-erythro ratio of about 1.

11. The method of any preceding claim, wherein the levoglucosanol has a threo-to-erythro ratio of less than 1.

12. The method of any preceding claim, wherein the levoglucosanol has a threo-to-erythro ratio of greater than 1.

14. The method of any preceding claim, wherein the method is conducted batch-wise or continuously.

DETAILED DESCRIPTION

Figure 1:
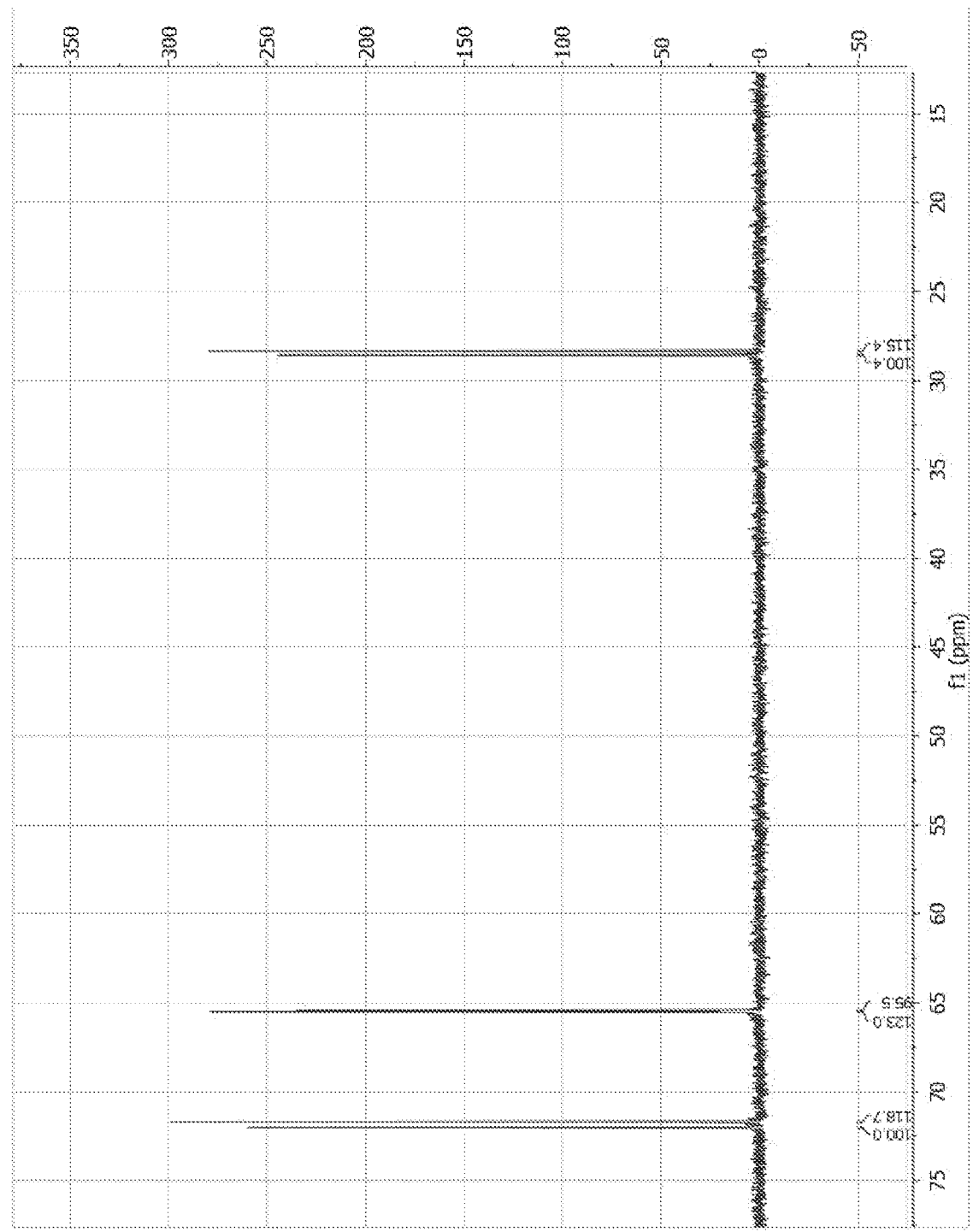
FIG. 1 is a quantitative $^{13}$C NMR spectrum of the product yielded by the disclosed process. The reaction, Lgol to tetrol, was 100%. Batch reaction of 10 mL of 0.9 wt % levoglucosanol in water using Pt/SiAl catalyst, 150° C., 500 psi $H_2$, 3 h reaction time, 100 mg 1% Pt/SiAl.

Abbreviations and Definitions:

The "noble metals" are defined herein as ruthenium (Ru), rhodium (Rh), palladium (Pd), silver (Ag), rhenium (Re), osmium (Os), iridium (Ir), platinum (Pt), gold (Au), and mercury (Hg).

LGO=levoglucosenone. LGOL=levoglucosanol.

As used herein, catalyst "support" refers to a solid material having a substantially stable surface area at the stated reaction conditions. That is, the support has a surface area that is not substantially altered by the reaction conditions or altered in any way physically or chemically that affects the reaction. The catalyst support generally comprises one or more solid acid materials. Exemplary solid acids which can be utilized include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of alumina, zirconia, titania, hafnia, silica, tin oxide, niobia, carbon, and the like, zeolites, and mixtures of these. In preferred versions of the method, the support comprises aluminum and silicon, with platinum, palladium, rhodium, and/or rhenium deposited on the support. The oxides themselves (e.g., $ZrO_2$, $SnO_2$, $TiO_2$, etc.) which may optionally be doped with additional acid groups such as sulfonates may also be used as solid acid catalysts.

Further examples of suitable solid acid supports include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulphuric acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Preferred supports are refractory oxides having acid sites, such as (but not limited to) alumina, zirconia, titania, hafnia, phosphates, silica; and mixtures of these. The catalyst support material can be or can include rare earth-modified refractory metal oxides, where the rare earth may be any rare earth metal, for example, lanthanum or yttrium; and/or alkali earth metal-modified refractory oxides. Zeolites can also be used as supports. H-type zeolites are generally preferred, for example zeolites in the mordenite group or fine-pored zeolites such as zeolites X, Y and L, e.g., mordenite, erionite, chabazite, or faujasite. The supported catalysts disclosed herein can be in any shape or form now known or developed in the future, such as, but not limited to, granules, powder, beads, pills, pellets, flakes, cylinders, spheres, or other shapes.

Tetrol=1,2,5,6-hexanetetrol.
THFDM=tetrahydrofurandimethanol.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more," unless explicitly stated to the contrary. Unless expressly stated to the contrary, "or" refers to an inclusive "or." That is, a condition "A or B" is satisfied by any one of the following: A is true (or present) and B is false (or not present), A is false (or not present) and B is true (or present), and both A and B are true (or present).

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry. The terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus.

As used herein, the term "about" modifying the quantity of an ingredient or reactant, or the value of a variable, refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; through the limitations of the equipment used to measure variables such as time, temperature, and pressure, and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

Overview:

As shown in Scheme 1, polysaccharides (or cellulose) can be converted into levoglucosenone (LGO) via acid-catalyzed dehydration. LGO can then be catalytically reduced into the corresponding alcohol, levoglucosanol (LGOL). At the heart of the current method is a means to catalytically convert LGOL into 1,2,5,6-hexanetetrol ("tetrol"), without over-reacting the LGOL into downstream products such as tetrahydrofurandimethanol (THFDM) or 1,6-hexanediol.

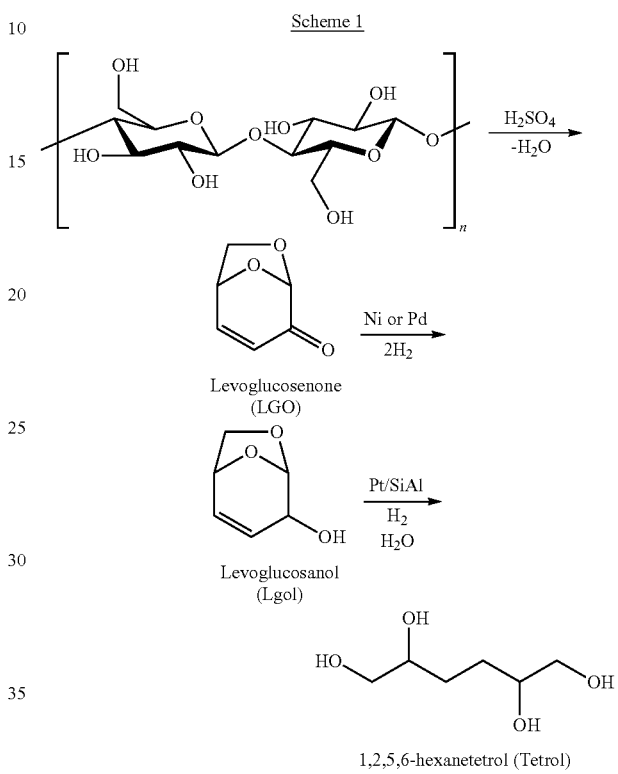

Scheme 1

The crux of the method is thus shown in Scheme 2. An aqueous reaction solution comprising levoglucosanol is contacted with a heterogeneous catalyst comprising a noble metal deposited on a support having acid sites in the presence of hydrogen ($H_2$). As noted earlier, the preferred reaction temperature is about 100° C. to about 175° C., and the preferred hydrogen partial pressure of from about 1 bar to about 50 bar (about 0.1 MPa to about 5 MPa).

Scheme 2

High yields of tetrol have been achieved using both dilute (0.9 wt %) and concentrated (22.5 wt %) Lgol solutions in water. See Table 1.

TABLE 1

Selectivity versus LGOL concentration

| Cat. | Lgol wt % | Time (h) | Lgol Conversion | Selectivities (%) | | |
|---|---|---|---|---|---|---|
| | | | | Tetrol | THFDM | Total |
| 1% Pt/SiAl | 0.90 | 3 | 90% | 94% | 3% | 97% |
| 5% Pt/SiAl | 22.5 | 17 | 100% | 86% | 7% | 93% |

Conditions: 150 C, 500 psi $H_2$, 100 mg catalyst, 10 mL Lgol in water solvent.

Levoglucosenone can also be directly upgraded in one pot to tetrol. In batch reactions using 0.9 wt % LGO in water over 1% Pt/SiAl, 500 psi $H_2$ (34 bar) at 150° C. shows 90% tetrol yield, with THFDM as a side-product. See Scheme 3.

Scheme 3

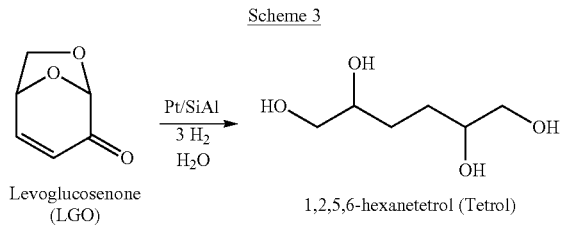 [SMILES: O=C1C=CC2COC1O2 ; "3 H2H2O" ; OCC(O)CCC(O)CO]

Levoglucosenone (LGO)    1,2,5,6-hexanetetrol (Tetrol)

Platinum is the preferred catalyst. But other noble metals may also be used, as shown in Table 2. As shown in Table 2, platinum, palladium, rhodium, and ruthenium all function with acceptable results, although platinum clearly provides superior results.

See also FIG. 1, which is the quantitative $^{13}$C NMR spectrum of the product yielded by the reaction batch reaction of 10 mL of 0.9 wt % levoglucosanol in water using Pt/SiAl catalyst, 150° C., 500 psi $H_2$, 3 h reaction time, 100 mg 1% Pt/SiAl. Yield to tetrol was nearly quantitative (93%).

TABLE 2

Conversion and Selectivity to Tetrol and THFDM with different metal catalysts

| Cat. | Lgol Conversion | Selectivities (%) | | | |
|---|---|---|---|---|---|
| | | Tetrol | Hemiketal-ketone | THFDM | Total |
| 1% Pt/SiAl | 90% | 94% | | 3% | 97% |
| 1% Pd/SiAl | 93% | 52% | | 41% | 92% |
| 1% Ru/SiAl | 58% | 91% | | 0% | 91% |
| 1% Rh/SiAl | 96% | 35% | 54% | 11% | 100% |

Effect of Metal and Acid Sites (Proposed Mechanism):

Without being limited to any specific reaction mechanism or underlying chemical phenomena, a putative mechanism for the reaction is provided in Scheme 4. Of particular note in proposing this mechanism is that the reaction does not occur when a metal supported on a non-acidic support is used for the catalyst. When the same reaction is carried out with a solid acid catalyst (SiAl) in the absence of a metal, $^{13}$C NMR and ESI-MS showed that a hemiketal-ketone are major intermediates, with hemiacetal as a minor intermediate (see Scheme 4). Hydrogenation of the intermediates over a metal catalyst then yields tetrol as a major product (see Table 3). Thus, it is proposed that the reaction proceeds by an acid-catalyzed C—O cleavage followed by the metal-catalyzed hydrogenation of the intermediate to yield tetrol. The reaction can also be carried out over a physical mixture of metal and acid catalysts (see Table 3). LGOL+homogeneous $H_2SO_4$ also yields a hemiacetal intermediate, and hydrogenation of this intermediate shows a lower selectivity to tetrol (~50%).

Figure 2:
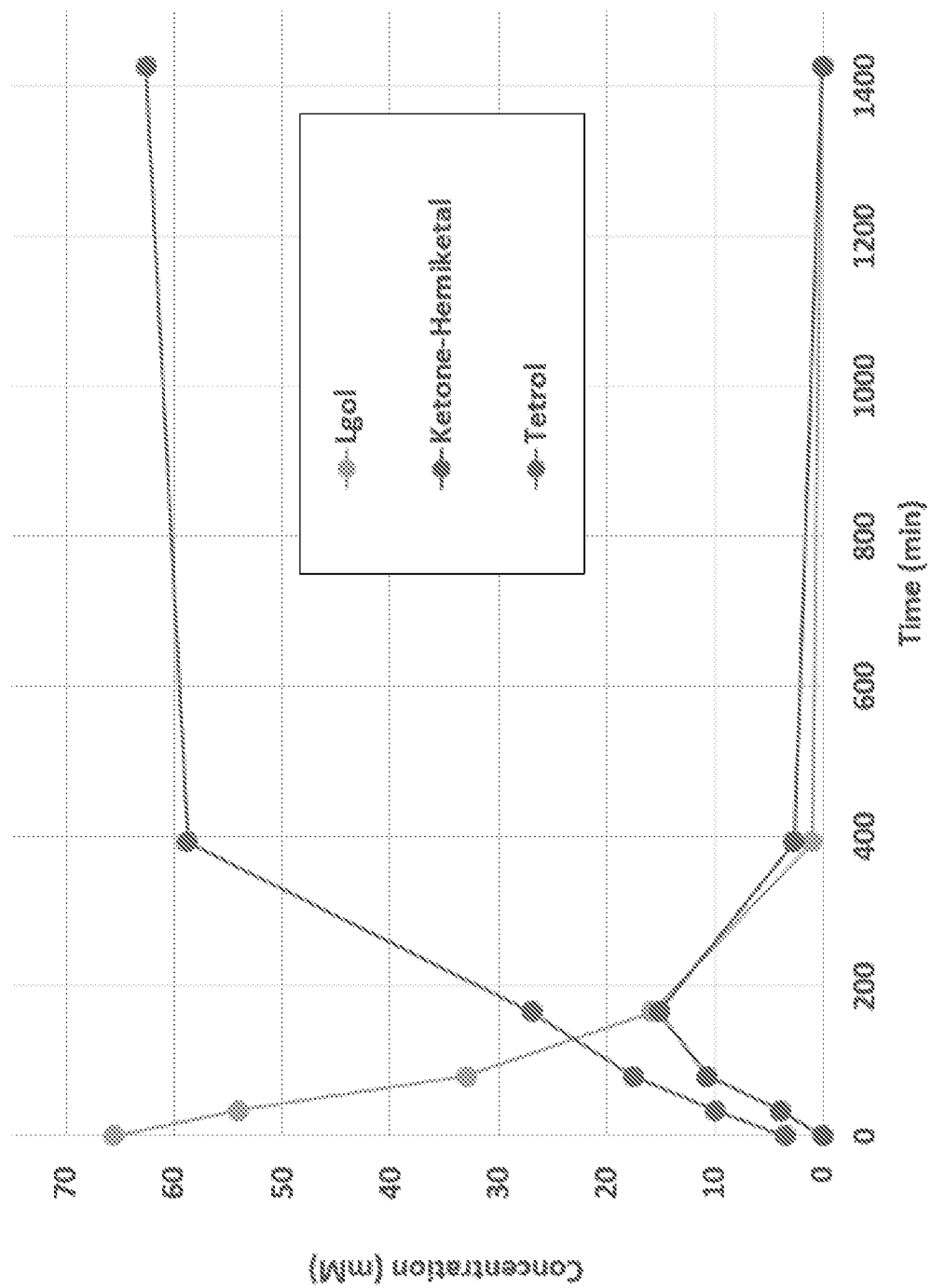
FIG. 2 is graph depicting the concentrations of reactant and products over time in a batch reactor with dip-tube sampling. Batch reaction of 60 mL of 0.9 wt % levoglucosanol in water using Pt/SiAl catalyst, 150° C., 500 psi $H_2$, 360 mg 1% Pt/SiAl.

As shown in FIG. 2, Lgol is converted to Tetrol via a ketone-hemiketal intermediate which is present at short reaction times. Once 100% conversion of Lgol is achieved (by 400 minutes), there is no decrease in yield of Tetrol up to 1400 minutes, indicating that Tetrol is stable (i.e., Tetrol does not undergo further reactions) under these conditions.

TABLE 3

Conversion and selectivity for different metal-acid catalyst configurations

| Cat. | Time (h) | Lgol Conversion | Selectivities (%) | | | |
|---|---|---|---|---|---|---|
| | | | Tetrol | Hemiketal-Ketone | THFDM | Total |
| 1% Pt/SiAl | 3 | 90% | 94% | 0% | 3% | 97% |
| Phys mix: 1% Pt/SiO2 & SiAl | 3 | 100% | 85% | 0% | 8% | 93% |
| SiAl, then Pt/SiO2 | 3, 3 | 74% | 58% | 17% | 15% | 89% |
| H2SO4, then Pt/SiO2* | 0.25, 3 | 71% | 51% | | 5% | 56% |

Conditions: 150 C., 500 psi H2, 100 mg catalyst, 10 mL 0.9 wt % Lgol in water solvent.

*for $H_2SO_4$ reaction, the $H_2SO_4$ concentration was 50 mM and the reaction was carried out at 130° C. for 0.25 h.

Scheme 4

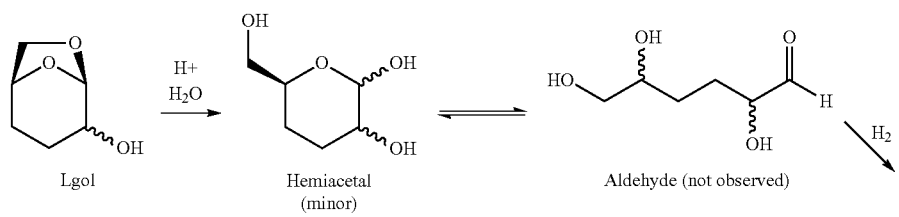

Lgol    Hemiacetal (minor)    Aldehyde (not observed)

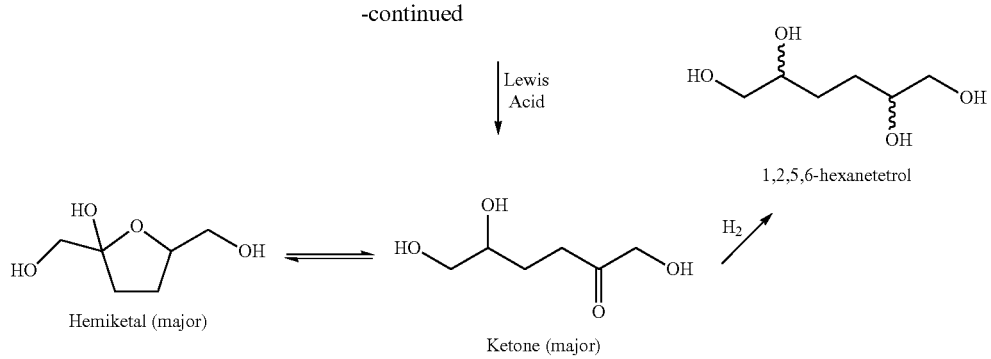

Control Over Tetrol Stereochemistry:

The method is also tunable to yield diastereomerically enriched tetrol by starting with diastereomerically enriched LGOL. See Scheme 5. By altering the ratio of threo to erytho isomers in the reactant, the cis/trans ratio of the product tetrol is likewise altered.

The LGOL threo/erythro ratio can be varied by hydrogenating cyrene with different catalysts to yield a diastereomerically enriched reactant solution. When the threo-to-erythro ratio of the reactant LGOL is altered to something other than 1:1 (either higher or lower), the cis/trans ratio of the product tetrol is also impacted. See Table 4. The yields in these experiments were 85-91%.

Scheme 5

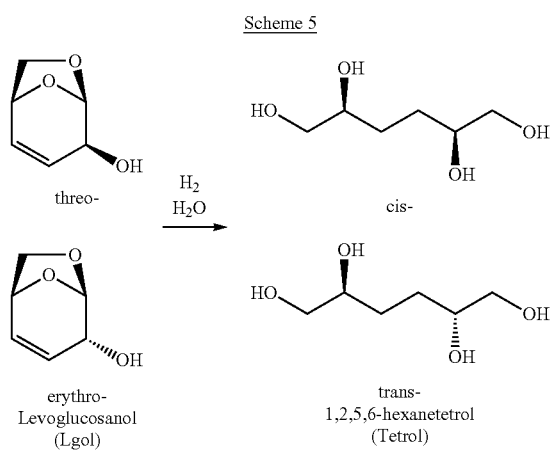 [SMILES: O[C@H]1C=C[C@H]2CO[C@@H]1O2 ; OC[C@@H](O)CC[C@H](O)CO ; O[C@@H]1C=C[C@H]2CO[C@@H]1O2 ; OC[C@@H](O)CC[C@@H](O)CO]

TABLE 4

Effect of Lgol stereochemistry on Tetrol stereochemistry

| Cat. | Lgol threo/erythro | Tetrol cis/trans |
| --- | --- | --- |
| 1% Pt/SiAl | 1.4 | 1.2 |
| 5% Pt/SiAl | 4.3 | 2.8 |

The data shown in Table 4 was generated using 10 mL of 0.9 wt % LGOL/water, which was converted to tetrol in a batch reactor using 100 mg Pt/SiAl catalyst, at 150° C., 500 psi $H_2$, and a 3 h reaction time. The tetrol cis/trans ratio was determined by 13C NMR.

What is claimed is:

1. A method of making of 1,2,5,6-hexanetetrol, the method comprising:
contacting a solution comprising levoglucosenone, dihydrolevoglucosenone, or levoglucosanol, or mixtures thereof and water, with a catalyst containing metal sites and acid sites, at temperature of from about 100° C. to about 175° C., and a hydrogen partial pressure of from about 1 bar to about 50 bar (about 0.1 MPa to about 5 MPa), and for a time wherein at least a portion of the levoglucosenone, dihydrolevoglucosenone, or levoglucosanol, or mixtures thereof is converted into 1,2,5,6-hexanetetrol.

2. The method of claim 1, wherein the catalyst comprises a metal selected from the group consisting of Ru, Rh, Pd, Os, Jr, Pt, Au, Ag, Cu, Co, Fe, and Ni.

3. The method of claim 1, wherein the catalyst comprises a noble metal selected from the group consisting of Ru, Rh, Pd, and Pt.

4. The method of claim 1, wherein the catalyst comprises a noble metal that is platinum.

5. The method of any one of claims 1 to 4, wherein the pressure is from about 20 to about 45 bar.

6. The method of claim 5, wherein the pressure is from about 30 to about 40 bar.

7. The method of claim 1, wherein the acid catalyst comprises a mineral acid selected from the group consisting of sulfuric acid, hydrochloric acid, nitric acid, and phosphoric acid, and solid acidic supports selected from the group consisting of alumina, zirconia, titania, hafnia, silica, zirconia-phosphate, titania-phosphate, zirconia-tungsten, titania-tungsten, zeolites, and mixtures of these.

8. The method of claim 1, wherein the catalyst comprises aluminum and silicon.

9. The method of claim 1, wherein the catalyst comprises platinum deposited on a support.

10. The method of claim 1, wherein the solution comprises levoglucosanol having a threo-to-erythro ratio of about 1.

11. The method of claim 1, wherein the solution comprises levoglucosanol having a threo-to-erythro ratio of less than 1.

12. The method of claim 1, wherein the solution comprises levoglucosanol having a threo-to-erythro ratio of greater than 1.

13. The method of claim 1, wherein the method is conducted batch-wise or continuously.

* * * * *